United States Patent [19]

Wolff

[11] 4,106,083
[45] Aug. 8, 1978

[54] REFLECTOR FOR USE IN SUNLAMPS OR THE LIKE

[76] Inventor: Friedrich Wolff, Bertholdstrasse 18, Frankfurt, Fed. Rep. of Germany

[21] Appl. No.: 716,254

[22] Filed: Aug. 20, 1976

[30] Foreign Application Priority Data

Aug. 26, 1975 [DE] Fed. Rep. of Germany ....... 2537855

[51] Int. Cl.² .............................................. F21V 7/00
[52] U.S. Cl. .................................... 362/217; 219/349; 350/294; 362/297; 362/346
[58] Field of Search ............ 240/103, 103 R, 51.11 R, 240/41.35 R, 41.35 C, 41.35 E, 11.4 R; 72/363, 379; 350/294; 219/343, 347, 349; 362/217, 290, 297, 346, 347

[56] References Cited

U.S. PATENT DOCUMENTS

| | | | |
|---|---|---|---|
| 3,152,765 | 10/1964 | Wohlers | 362/217 |
| 3,363,093 | 1/1968 | Schmitt | 240/103 R X |
| 3,746,854 | 8/1973 | Brass | 362/217 |
| 3,829,677 | 8/1974 | Dellano | 240/51.11 R |
| 4,006,355 | 2/1977 | Shemitz et al. | 240/103 R X |
| 4,053,766 | 10/1977 | Brass | 362/297 X |

Primary Examiner—Richard A. Wintercorn
Attorney, Agent, or Firm—Peter K. Kontler

[57] ABSTRACT

A trough-shaped reflector for use with rod-shaped sources of ultraviolet radiation in sunlamps has a rear wall behind the source and two side walls which flank the source and define therewith two narrow gaps. The front portions of the side walls are parallel to each other and extend forwardly beyond the source. The front surface of the rear wall has two concave portions which reflect rays into the respective gaps, and the rear portions of the side walls have parallel, zig-zag shaped or concave inner surfaces. The reflector can be made of a rectangular blank of sheet metal by imparting to the median portion of the blank a semicylindrical shape, by notching the outer side of the median portion midway between the marginal portions of the resulting preform, and by notching the inner side of the median portion at both sides of the notch in the outer side.

34 Claims, 5 Drawing Figures

REFLECTOR FOR USE IN SUNLAMPS OR THE LIKE

BACKGROUND OF THE INVENTION

The present invention relates to artificial sunlight lamps or sunlamps in general, and more particularly to improvements in reflectors which can be used in sunlamps to direct rays issuing from suitable sources of radiation (especially sources of ultraviolet rays) in a desired direction. Still more particularly, the invention relates to improvements in reflectors which can be used in connection with substantially rod-shaped sources of radiation.

OBJECTS AND SUMMARY OF THE INVENTION

An object of the invention is to provide a reflector which is capable of insuring the development of a high-density radiation field at a selected distance from the radiation source.

Another object of the invention is to provide a reflector which, when used with a radiation source of given intensity, can insure the development of a radiation field whose density greatly exceeds the densities of radiation fields developing when the same source is used with a conventional reflector.

A further object of the invention is to provide a relatively simple, inexpensive and eye-pleasing reflector which can be used with advantage in floor models or table models of sunlamps for tanning and/or therapeutical purposes.

An additional object of the invention is to provide a reflector which can be used with many existing sources of infrared and/or ultraviolet radiation.

An ancillary object of the invention is to provide a one-piece reflector which can be mass-produced by resorting to readily available machinery.

One feature of the invention resides in the provision of a reflector which can be used in combination with rod-shaped radiation sources, particularly with sources of infrared and/or ultraviolet radiation. The reflector is substantially trough-shaped and has two halves which are substantially mirror symmetrical to each other with reference to a plane which includes the axis of the radiation source. The reflector comprises a rear wall which is located behind the rod-shaped source and two side walls which extend forwardly from the rear wall and flank the source. The side walls have front portions which define an exit opening for the rays issuing from the source, and the inner surfaces of the front portions of the side walls are preferably parallel to each other. Such front portions may extend forwardly and well beyond the source to reduce the amount of stray radiation, and each side wall defines with the source a relatively narrow gap for propagation of rays which are reflected by the front surface of the rear wall, by the inner surfaces of the rear portions of the side walls, by intermediate walls between the rear wall and the side walls and/or by auxiliary reflectors which can be mounted in the gaps adjacent to the envelope of the light source.

The method of making one type of the improved reflector comprises the steps of bending the median portion of a substantially rectangular metallic blank to thus convert the blank into a trough-shaped preform with a substantially semicylindrical central section and two substantially parallel marginal sections, and impressing into the outer side of the central section a longitudinally extending notch or depression substantially midway between the marginal sections. The method may further comprise the step of impressing into the inner side of the central section two additional notches or depressions extending in parallelism with and located at the opposite sides of the notch in the outer side of the central section.

The novel features which are considered as characteristic of the invention are set forth in particular in the appended claims. The improved reflector itself, however, both as to its construction and the mode of making the same, together with additional features and advantages thereof, will be best understood upon perusal of the following detailed description of certain specific embodiments with reference to the accompanying drawing.

DESCRIPTION OF THE PREFERRED EMBODIMENTS

Figure 1:
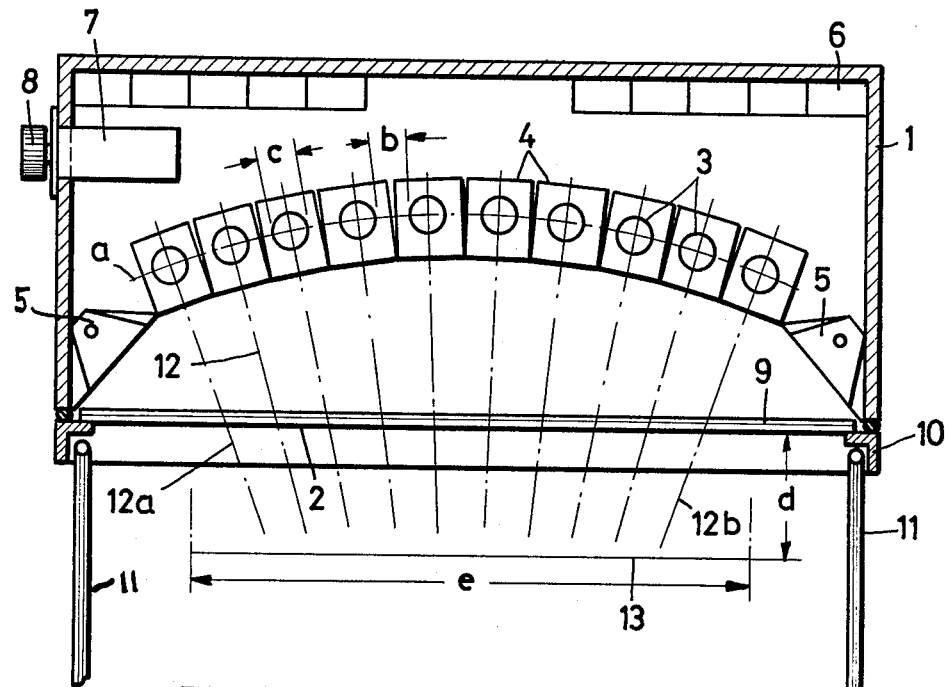
FIG. 1 is a diagrammatic horizontal sectional view of an upright floor-mounted sunlamp having a battery of rod-shaped radiation sources and an equal number of reflectors embodying one form of the invention.

FIG. 1 shows a floor-type sunlamp including a housing 1 the front side of which has a window 2 for rays issuing from a battery of ten upright rod-shaped radiation sources 3. The radiation sources 3 (hereinafter called sources for short) are parallel to each other and their axes are disposed in a common arcuate plane $a$ which is located behind the window 2. Each source 3 is assumed to constitute or include a low-pressure mercury lamp having a length of 150 centimeters. In accordance with a feature of the invention, each source 3 is associated with and partially surrounded by a discrete trough-shaped reflector 4 which is constructed and assembled in a manner as shown in FIG. 2, 3, 4 or 5. The battery of sources 3 and associated reflectors 4 is flanked by two infrared heaters 5 each of which may comprise an electrically heated rod consisting of silicon carbide. The heaters 5 are optional.

The housing 1 further contains conventional auxiliary equipment 6 for the sources (e.g., timers) and controls 7 including a starter knob 8 which is accessible at the outer side of the housing. The window 2 contains a plate-like filter 9 which intercepts all or nearly all radiation within certain ranges of wavelengths (preferably the radiation within the so-called UVB and UVC ranges). The filter 9 is optional because each source 3 may comprise a tubular envelope (e.g., a glass envelope) having radiation-intercepting properties which match or closely approximate those of the filter 9.

It will be noted that, with the exception of the knob 8, all essential component parts of the sunlamp are installed in the interior of the housing 1. The latter further comprises a frame 10 for the filter 9 and pivotable doors 11 which are mounted on the frame 10 and are movable between the illustrated open positions (window 2 exposed) and closed positions in which the window 2 is concealed. The housing 1, inclusive of the frame 10 and doors 11, may resemble a cabinet or another piece of furniture, e.g., a cabinet not unlike the housing of a television receiver, and may be provided with wheels to facilitate transport to different locales of use or to storage. The doors 11 and/or other parts of the housing 1 may be suitably decorated so that the sunlamp can constitute or resemble a piece of furniture which enhances the appearance of the room where the sunlamp is put to use or stored, regardless of whether the doors 11 are held in open or closed positions.

The distance $b$ between two neighboring sources 3 equals or approximates 70 percent of the diameter $c$ of a source. Thus, the distance between the central symmetry planes 12 of neighboring sources 3 (these symmetry planes are normal to the plane $a$) equals $b+c$. The central symmetry planes 12a and 12b of the two outermost sources 3 make an angle of less than 80°, e.g., an angle of 45°. Each reflector 4 has two halves which are mirror symmetrical to each other with reference to the respective plane 12, and each such plane includes the axis of the corresponding source 3.

The sunlamp of FIG. 1 can produce, at a distance $d = 10$ centimeters from the window 2, a radiation field 13 having a width $e = 70$ centimeters and a height (as measured at right angles to the plane of FIG. 1) of 150 centimeters. The density of the so-called UVA radiation in the field 13 is approximately 12 mw/cm$^2$. The density decreases in directions toward the doors 11 but does not drop below 4 mw/cm$^2$. In fact, the density substantially exceeds 4 mw/cm$^2$ in the region of this symmetry planes 12a, 12b.

If desired, the axes of the sources 3 can be located in a plane which is exactly parallel to the plane of the filter 9. Furthermore, the sources 3 may be staggered to form a zig-zag formation or another suitable array. If the sources 3 form a zig-zag array, each section of such array may include a row of two or three parallel sources.

Figure 2:
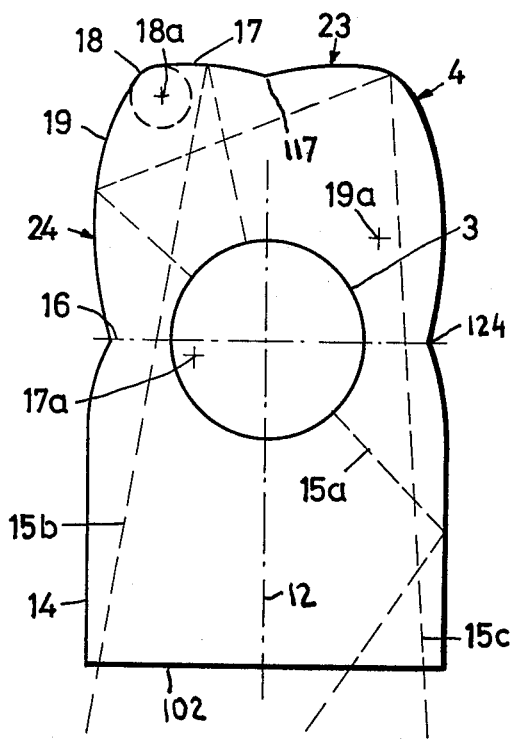
FIG. 2 is an enlarged view of a detail in FIG. 1, showing a single radiation source and the associated reflector.

FIG. 2 shows, in a horizontal sectional view, one of the sources 3 and the associated trough-shaped reflector 4. The reflector 4 has two halves which are mirror symmetrical to each other with reference to the plane 12 which includes the axis of the source 3. More specifically, the reflector 4 of FIG. 2 comprises a rear wall 23 and two side walls 24 which extend forwardly of the respective marginal portions of the rear wall 23 and define with the source 3 two relatively narrow gaps or clearances 16. The front portions 14 of the side walls 24 have parallel inner surfaces which face each other, and these front portions extend forwardly well beyond the source 3, i.e., the entire source is received in the interior of the reflector 4 so that radiation can issue only by way of an exit opening 102 which extends between the foremost parts of the front portions 14. The feature that the front portions 14 extend well beyond the source 3 insures that certain rays (see the ray 15a) which issue from the source and impinge upon the inner surfaces of the front portions 14 are reflected in a desired direction, i.e., that the width of the radiation field which is produced by the assembly of parts 3 and 4 can be determined with a high degree of accuracy.

The reflector 4 of FIG. 2 further comprises two relatively narrow intermediate walls 18 which extend between the rear wall 23 and the respective side walls 24. The configuration of the front surface of the rear wall 23, of the inner surfaces of intermediate walls 18, and of the inner surfaces of rear portions 19 of side walls 24 is selected in such a way that the majority of rays which impinge upon such surfaces are directed forwardly into the gaps 16 and thence toward and through the opening 102. To this end, the front surface of the rear wall 23 comprises two concave portions 17 located at the opposite sides of the symmetry plane 12 and having equal radii of curvature which are larger than the radii of curvatures of concave inner surfaces of the intermediate walls 18. The concave portions 17 are separated from each other by a ridge 117 which extends forwardly toward the source 3, which is located in or close to the plane 112, and which is parallel to the axis of the source 3. The inner surfaces of the rear portions 19 of the side walls 24 are also concave and face each other. The center of curvature of the lefthand concave surface portion 17 is shown at 17a, the center of curvature of the concave inner surface of one of the intermediate walls 18 is shown at 18a, and the center of curvature of the concave surface of the left-hand rear portion 19 is shown at 19a. The radii of curvature of the surface portions 17 (see the center 17a) are preferably identical with the radii of curvature of the concave surfaces of rear portions 19 (see the center 19a), and each such radius is a multiple of the radius of curvature of the concave inner surface of an intermediate wall 18 (see the center 18a). The inner surfaces of the front portions 14 of the side walls 24 are parallel to each other. One of the rays which are reflected by the concave portions 17 of the front surface of the rear wall 23 and enter directly into the respective gap 16 is shown at 15b. The reference character 15c denotes a ray which is reflected by the concave inner surface of the left-hand rear portion 19 against the concave inner surface of the right-hand intermediate wall 18 and thence into the respective gap 16. The curvature of portions 17 of the front surface of the rear wall 23 is such that a substantial (and preferably major) percentage of rays which impinge upon the rear wall 23 is directed into the two gaps 16.

The side walls 24 may but need not be formed with more or less pronounced edges 124 between the front portions 14 and the respective rear portions 19. Such edges are preferably located in the region of the narrowest portions of the respective gaps 16. It has been found that a reflector which is constructed and configurated in a manner as shown in FIG. 2 is capable of directing nearly all rays, which issue from the source 3 behind the edges 124, into the respective gaps 16 to thus insure that the combination of parts 3 and 4 establishes a high-density portion of the radiation field 13 shown in FIG. 1.

The manner in which at least the inner side of the reflector 4 may be treated to insure satisfactory reflection of radiation is known in the art of sunlamps.

An important advantage of the improved reflector is that it can produce a radiation field (see 13 in FIG. 1) of surprisingly high density. This is attributed to the fact that the configuration of surfaces surrounding the space for the radiation source 3 is selected with a view to insure single or repeated reflection of a high percentage of rays which issue from the source in a direction away from the exit opening 102 whereby the reflected rays pass through and beyond the gaps 16 and toward the opening 102. Another reason for the surprisingly high density of the radiation field is that the opening 102 is relatively narrow, especially when compared with the exit openings of conventional reflectors for radiation sources of sunlamps or the like. The trough-shaped configuration of the reflector 4 also contributes to a highly satisfactory orientation of rays which advance toward, through and beyond the exit opening. Moreover, the aforedescribed configuration of the reflector insures that the density of radiation in front of the exit opening is uniform or practically uniform along the full width of the opening.

The feature that at least the front portions of the side walls 24 are parallel or nearly parallel to each other (i.e., that the width of the opening 102 equals or approximates the maximum distance between the side walls 24) contributes to compactness of the reflector as well as to a desirable orientation of rays which issue from the opening. Compactness is important and desirable in all or nearly all floor and/or table models of sunlamps or the like, especially when the sunlamp comprises a large number of radiation sources which must be accommodated in a relatively small housing or frame.

Another important advantage of the reflector is that the front portions 14 of its side walls 24 extend forwardly of and preferably well beyond the foremost part of the source 3. It has been found that the percentage of stray radiation is reduced considerably even if the side walls extend only slightly beyond the foremost part of the source, especially if the inner surfaces of the front portions of the side walls are parallel or nearly parallel to each other, i.e., if the exit opening is relatively narrow. The width of the gaps 16 is preferably less than the diameter $c$ of a source 3, most preferably less than $c/2$. This also contributes to highly satisfactory density of the field 13 in front of the reflectors; moreover such selection of the width of the gaps 16 contributes to compactness of the reflector.

The aforediscussed configuration of the front surface of the rear wall 23 also contributes to more satisfactory density of the field 13 because the concave portions of such front surface are capable of reflecting a high percentage of rays into the respective gaps 16 and thence into the exit opening 102 in spite of the fact that the width of the gaps is preferably less than the radius of the associated source 3. The concave portions of the front surface of the rear wall 23 can reflect rays directly into the nearest gaps 16 or against the inner surfaces of the side walls 24, always in such a way that the rays can pass through the gaps and toward the exit opening.

The concave inner surfaces of intermediate walls 18 also contribute to satisfactory density of the field 13, i.e., to a high radiation output. This is due to the fact that such inner surfaces can reflect the rays 15c directly into the respective gaps 16 or against the inner surfaces of the front portions 14 of side walls 23 whence the rays 15c advance toward and beyond the exit opening. The curvature of concave inner surfaces of the rear portions 19 and of the concave inner surfaces of intermediate walls 18 is such that these surfaces reflect a very high percentage of rays 15c directly into the gaps 16.

Figures 3, 4:
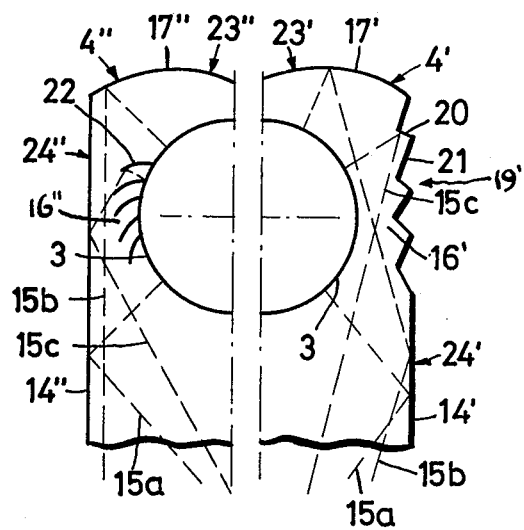
FIG. 3 is a fragmentary transverse sectional view of a modified reflector.
FIG. 4 is a similar fragmentary transverse sectional view of a third reflector.

FIG. 3 shows a portion of a rod-shaped radiation source 3 and the right-hand half of a modified trough-shaped reflector 4'. All such parts of this reflector which are identical with or clearly analogous to the corresponding parts of the reflector 4 are denoted by similar reference characters each followed by a prime. The rear portions 19' of the side walls 24' are substantially zig-zag shaped and consist of mutually inclined sections 20 and 21. The inclination of sections 20 is such that a ray 15c which impinges thereagainst is directed toward and into the respective gap 16' and that the ray is substantially parallel to the section 21 located in front of the respective section 20. Each zig-zag shaped rear portion 19' may extend to or even beyond the narrowest portion of the respective gap 16'. The manner in which the rays 15a and 15b are reflected is the same as described in connection with FIG. 2. Each ray 15b may pass directly toward and through the respective gap 16 or 16' or is reflected by the inner surface of the respective front portion 14 or 14'.

The sections 21 can reflect rays which are reflected by the front surface of the rear wall 23'.

Referring to FIG. 4, there is shown a portion of a rodshaped radiation source 3 and the left-hand half of a third troughshaped reflector 4''. All such parts of the reflector 4'' which are identical with or clearly analogous to the corresponding parts of the reflector 4 are denoted by similar reference characters each followed by two primes. The side walls 24'' have inner surfaces which are parallel to each other all the way to the rear wall 23''. The curvature of each concave portion 17'' of the front surface of rear wall 23'' is somewhat more pronounced than that of a portion 17 or 17'. The manner in which the rays 15a and 15b are reflected by the walls 23'' and 24'' is indicated by broken lines.

The structure of FIG. 4 further comprises additional or auxiliary reflectors 22 which are located in the respective gaps 16'' and have concave front surfaces. The auxiliary reflectors 22 are immediately adjacent to the envelope of the source 3. A ray 15c which issues from the source 3 and is reflected by the concave front surface of an auxiliary reflector 22 bypasses the tip of the reflector 22 which is located in front of such concave surface so that the reflected ray 15c can enter the respective gap 16''.

Figure 5:
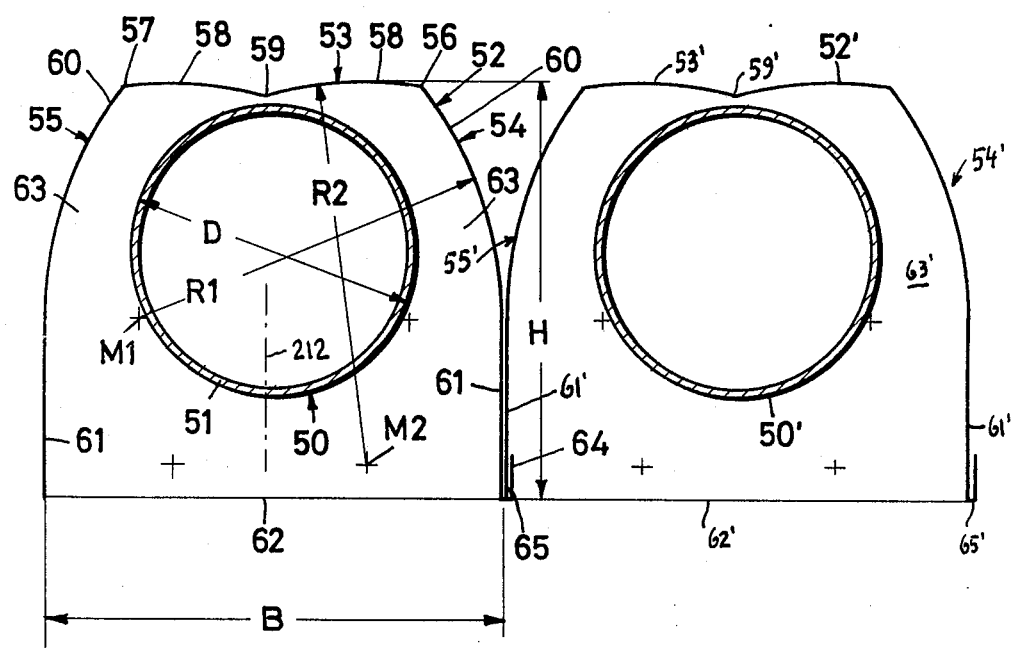
FIG. 5 is a transverse sectional view of two parallel radiation sources and of two associated reflectors each of which is constructed in accordance with a further embodiment of the invention.

FIG. 5 shows two neighboring parallel rod-shaped radiation sources 50, 50' and the associated trough-shaped reflectors 52, 52'. The two radiation sources and the two reflectors are respectively identical with each other. The source 50 comprises a cylindrical envelope 51 which permits penetration of UVA radiation but intercepts radiation in the UVB and UVC ranges of wavelengths. This source is a low-pressure mercury lamp. The wavelength range of UVA radiation is between 315 and 380 nm, the range of UVB radiation is between 280 and 315 nm, and the range of UVC radiation is between 200 and 280 nm.

The trough-shaped reflector 52 has two halves which are mirror symmetrical to each other with reference to a plane 212 which includes the axis of the source 50 and is parallel to the flat inner surfaces of the front portions 61 of the two side walls 54, 55. The exit opening is shown at 62 and the two gaps are shown at 63. The rear portions 60 of the side walls 54, 55 have concave inner surfaces which face each other and merge gradually into the flat inner surfaces of the respective front portions 61. The rear wall 53 of the reflector 52 has a front surface which faces the source 50 and the opening 62 and includes two concave portions 58 separated from each other by a depression or notch 59 which is immediately or very closely adjacent to the source 50. The median portion of the rear wall 53 can practically touch the nearest portion of the envelope 51. The rear portions 60 of the side walls 54, 55 define with the rear wall 53 two more or less pronounced straight edges 56, 57 which are parallel to the axis of the source 50 and are located at the opposite sides of the notch 59.

The width B of the exit opening 62 is less than three D, preferably less than 2D and most preferably about 1.5D (D is the diameter of the source 50). In FIG. 5, the width B is assumed to equal or approximate 1.5D and, therefore, the width of each gap 63 is approximately ¼D, i.e., less than the radius of the source 50. The depth H of the reflector 52 (i.e., the maximum distance between the opening 62 and the rear wall 53) exceeds the diameter D by 15 to 80 percent, preferably by a little more than 30 percent.

The radius of curvature of the concave inner surface of the rear portion 60 of the side wall 54 is shown at R1, and the radius of curvature of the right-hand concave portion of the front surface of the rear wall 53 is shown at R2. The centers of curvature of surfaces having the radii R1 and R2 are respectively shown at M1 and M2. The radius R1 equals the radius R2. This is desirable and advantageous because the reflector 52 can be mmanufactured at a relatively low cost by resorting to a simple method which includes the first step of forming an elongated rectangular blank of sheet metal or other suitable material. The median portion of the blank (i.e., the portion which is disposed midway between the two longer sides) is thereupon bent in a suitable machine of conventional design to convert the blank into a trough-shaped preform having a semicylindrical central section (including the rear wall 53 and the rear portions 60 of the side walls 54, 55) and two marginal sections which constitute the front portions 61 of the finished reflector 52. The outer side of the semicylindrical section is then provided with the depression or notch 59 which can be impressed therein by any conventional instrumentality or instrumentalities, and the inner side of the semicylindrical section is provided with two parallel notches which flank the notch 59 and cause the formation of edges 56 and 57 between the side walls 54, 55 and the rear wall 53 of the finished reflector 52. The radius of the aforementioned cylindrical central section of the preform equals $\frac{1}{2}R1 = \frac{1}{2}R2$. The three notches can be formed in a simultaneous operation, or the edges 56, 57 can be formed prior or subsequent to impression of the notch 59 into the outer side of the central section.

The reflectors of FIG. 5 exhibit the advantage that the depth H does not appreciably exceed the diameter D even if the front portions of the side walls extend well beyond the source. In fact, the width of the clearance between the central notch 59 or 59' in the rear wall 53 or 53' and the source 50 or 50' can be so small that the difference between D and H practically equals the extent to which the front portions 61 and 61' extend forwardly beyond the respective sources. While the front portions 61 or 61' can flare slightly outwardly in a direction toward the respective exit openings, the provision of parallel front portions is desirable for convenience of assembly of plural reflectors side-by-side as well as because such construction contributes to a reduction of the maximum width (B) of the reflectors. A reduction in the width B and depth H is desirable on the additional ground that the reflectors can be produced at a lower cost since the quantity of starting material of the reflectors is only a fraction of the quantity which is needed to produce a conventional reflector.

The aforementioned method also contributes to lower cost of the reflectors which are shown in FIG. 5. Since the reflectors are of identical size and shape, the same tool or tools can be used for the conversion of flat sheet-like blanks into preforms and thereupon into finished reflectors. Such method can be resorted to for mass-production of the improved reflectors.

The foremost part of the front portion 61 of the side wall 54 defines a socket 65 for the foremost part of the front portion 61' of the left-hand side wall 55' of the reflector 52'. The socket 65 is obtained by bending one-half 64 of the foremost part of the right-hand front portion 61 outwardly and into a position of parallelism with the remaining half of such foremost part so that the two halves define a relatively narrow slot for reception of the adjacent portion of the reflector 52'. The socket of the front portion 61' of the right-hand side wall 54' of the reflector 52' is shown at 65'. Such sockets allow for rapid and reproducible assembly of several reflectors, one next to the other, to form a battery of reflectors resembling those shown in FIG. 1.

The rays which issue from the front half of the source 50 or 50' travel directly toward and through the respective exit opening 62 or 62', or are reflected (normally once) prior to reaching the respective gap 63 or 63' on their way toward the opening. The rays which issue from the rear half of the source 50 or 50' are reflected by the rear wall 53 or 53' and/or by the side walls 54, 55 or 54', 55' and reach the opening 62 or 62' by way of the respective gap or gaps 63 or 63'. Certain rays are reflected back into the source 50 or 50' and pass through the source on their way toward the opening 62 or 62'.

By way of example, the diameter D of the source 50 or 50' may equal 38 millimeters, the width B of each opening may equal 60 millimeters, the depth H may equal 50 millimeters, and the radius R1 or R2 may equal 48 millimeters.

The improved reflectors can be used with commercially available rod-shaped radiation sources. For example, the aforementioned low-pressure mercury lamps may include those known as TL/05 and TL/09 produced by Philips. Such fluorescent lamps are designed to emit radiation within a predetermined range of the spectrum. Of course, one can resort to other types of fluorescent lamps or to any other suitable type of rod-shaped radiation sources.

For example, a radiation source which can be used with the improved reflector may comprise an envelope (e.g., a cylindrical envelope made of glass) which transmits at least some radiation in a certain wavelength range. Many types of low-pressure mercury lamps exhibit such features. This contributes to a surprisingly high radiation output and affords even greater freedom in selection of the design of the associated reflector. For example, the width of the gaps between the radiation source and the side walls of the associated reflector can be reduced almost to zero so that the width of the exit opening is only slightly greater than the diameter of the radiation source.

A sunlamp which utilizes the improved reflector or reflectors may be designed as a table model with one radiation source or a small number of radiation sources and an equal number of reflectors, or as a floor, wall or ceiling model with a substantial number of sources and reflectors (e.g., ten as shown in FIG. 1) so that the radiation field is large enough for exposure of the entire body of an adult to ultraviolet or infrared radiation.

The term "nm" (nanometer) denotes a unit of wavelength equal to 10 Angstroms.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

What is claimed is:

1. The combination of a rod-shaped radiation source, particularly a source of ultraviolet rays, with a substantially trough-shaped reflector having two halves which are substantially mirror symmetrical to each other with reference to a plane including the axis of said source, said reflector comprising a rear wall located behind said source and having a front surface facing said source, two side walls extending forwardly from said rear wall and flanking said source, said side walls having front portions which define an exit opening for the rays issuing from said source and rear portions adjacent to said rear wall and having concave inner surfaces facing each other, and two intermediate walls located between said rear portions and said rear wall and having concave inner surfaces merging into said front surface and into the inner surfaces of the respective rear portions, at least the major part of said source being located between said opening and said rear wall and each of said side walls defining with said source a relatively narrow gap.

2. The combination of claim 1, wherein the radii of curvature of said inner surfaces are such that a substantial percentage of rays issuing from said source and impinging upon the inner surfaces of said rear portions is reflected against the inner surfaces of the remote intermediate walls and thence into the respective gaps.

3. The combination of claim 2, wherein the radii of curvature of the inner surfaces of said intermediate walls are smaller than the radii of curvature of the inner surfaces of said rear portions.

4. The combination of claim 3, wherein said front surface of said rear wall includes two concave portions each of which merges into the inner surface of the respective intermediate wall.

5. The combination of a rod-shaped radiation source, particularly a source of ultraviolet rays, with a substantially trough-shaped reflector having two halves which are substantially mirror symmetrical to each other with reference to a plane including the axis of said source, said reflector comprising a rear wall located behind said source and two side walls extending forwardly from said rear wall and flanking said source, said side walls having front portions which define an exit opening for the rays issuing from said source and substantially zig-zag shaped rear portions located between said rear wall and the respective front portions, at least the major part of said source being located between said opening and said rear wall and each of said side walls defining with said source a relatively narrow gap.

6. The combination of claim 5 wherein said rear portions terminate in the general area of the respective gaps.

7. The combination of claim 1, wherein said rear portions have inner surfaces facing each other and including mutually inclined alternating first and second sections, the inclination of said first sections being such that the rays issuing from said source and impinging upon said first sections are reflected into the respective gaps and travel in substantial parallelism with the second sections located immediately in front of the respective first sections.

8. The combination of a rod-shaped radiation source, particularly a source of ultraviolet rays with (a) a substantially trough-shaped reflector having two halves which are substantially mirror symmetrical to each other with reference to a plane including the axis of said source, said reflector comprising a rear wall located behind said source and two side walls extending forwardly from said rear wall and flanking said source, said side walls having front portions which define an exit opening for the rays issuing from said source, at least the major part of said source being located between said opening and said rear wall and each of said side walls defining with said source a relatively narrow gap, and (b) auxiliary reflectors adjacent to said source and located in said gaps.

9. The combination of claim 8, wherein the auxiliary reflectors in each of said gaps are located one behind the other and have reflecting front surfaces facing toward said opening.

10. The combination of claim 9, wherein the configuration of the front surfaces of said auxiliary reflectors is such that rays issuing from said source and impinging upon said front surfaces are reflected into the respective gaps whereby the deflected rays bypass the auxiliary reflectors located in front of the respective front surfaces.

11. The combination of claim 10, wherein said front surfaces are concave and said rear wall has a front surface including two concave portions located at the opposite sides of said plane, at least a substantial percentage of rays issuing from said source and impinging upon said rear wall being reflected by said concave portions into the respective gaps.

12. The combination of a rod-shaped radiation source, particularly a source of ultraviolet rays with a substantially trough-shaped reflector having two halves which are substantially mirror symmetrical to each other with reference to a plane including the axis of said source, said reflector comprising a rear wall located behind said source and two side walls extending forwardly from said rear wall and flanking said source, said side walls having front portions which define an exit opening for the rays issuing from said source and have substantially parallel inner surfaces facing each other and rear portions having concave surfaces gradually merging into the inner surfaces of the respective front portions and converging toward each other in a direction toward said rear wall, at least the major part of said source being located between said opening and said rear wall and each of said side walls defining with said source a relatively narrow gap.

13. The combination of claim 12, wherein said front portions of said side walls extend forwardly beyond said source.

14. The combination of claim 12 wherein the minimum width of each of said gaps is less than the diameter of said rod-shaped source.

15. The combination of claim 12, wherein the minimum width of each of said gaps is less than the radius of said rod-shaped source.

16. The combination of claim 12, wherein said source emits rays at least in a first direction toward said rear wall and in a second direction toward said opening, said rear wall having a front surface which reflects rays emitted by said source in said first direction and the configuration of said front surface being such that at least a substantial percentage of light rays which are emitted in said first direction is reflected into said gaps.

17. The combination of claim 12, wherein said rear wall has a front surface facing said source and including two concave portions located at the opposite sides of said plane.

18. The combination of claim 17, wherein said rear wall comprises a ridge extending forwardly toward said source and located between said concave portions of said front surface, said ridge being substantially parallel to said source.

19. The combination of claim 12, wherein said rear wall comprises a median portion which is disposed in the region of said plane and is closely adjacent to said source.

20. The combination of claim 12, wherein the width of said opening, as considered in a direction from one of said front portions toward the other of said front portions, equals the maximum distance between said side walls.

21. The combination of claim 12, wherein the width of said opening is less than 3D wherein D is the diameter of said source.

22. The combination of claim 12, wherein the width of said opening is less than 2D.

23. The combination of claim 12, wherein the width of said opening is approximately 3r wherein r is the radius of said source.

24. The combination of claim 12, wherein the maximum distance between said opening and said rear wall exceeds the diameter of said source by 15 to 80 percent.

25. The combination of claim 24, wherein the maximum distance between said rear wall and said opening exceeds the diameter of said source by approximately 30 percent.

26. The combination of claim 12, wherein each of said rear portions defines with said rear wall an elongated edge extending in substantial parallelism with said source.

27. The combination of claim 12, wherein said source comprises an envelope which transmits at least a portion of radiation within a predetermined range of wavelengths.

28. The combination of a rod-shaped radiation source, particularly a source of ultraviolet rays, with a substantially trough-shaped reflector having two halves which are substantially mirror symmetrical to each other with reference to a plane including the axis of said source, said reflector comprising a rear wall located behind said source and having a front surface including two concave portions facing said source and two side walls extending forwardly from said rear wall and flanking said source, said side walls having front portions which define an exit opening for the rays issuing from said source and rear portions having concave inner surfaces facing each other, the radii of curvature of said concave portions closely approximating or being equal to the radii of curvature of said inner surfaces, at least the major part of said source being located between said opening and said rear wall and each of said side walls defining with said source a relatively narrow gap.

29. The combination of claim 28, wherein said front portions of said side walls are substantially parallel to each other.

30. The combination of claim 28, wherein said rear portions gradually approach each other in a direction toward said rear wall.

31. The combination of claim 28, wherein said concave portions and said inner surfaces are portions of cylindrical surfaces.

32. The combination of a rod-shaped radiation source, particularly a source of ultraviolet rays, with
    (a) a substantially trough-shaped reflector having two halves which are substantially mirror symmetrical to each other with reference to a plane including the axis of said source, said reflector comprising a rear wall located behind said source and two side walls extending forwardly from said rear wall and flanking said source, said side walls having front portions which define an exit opening for the rays issuing from said source, at least the major part of said source being located between said opening and said rear wall and each of said side walls defining with said source a relatively narrow gap,
    (b) at least one additional source of radiation parallel to said first mentioned source, and
    (c) a second reflector for said second source, said second reflector being identical with said first mentioned reflector and one side wall thereof being closely adjacent to one side wall of said first mentioned reflector.

33. The combination of claim 32 wherein one of said adjacent side walls has a socket for the foremost part of the front portion of the other of said adjacent side walls.

34. The combination of claim 33 wherein the foremost part of the front portion of said one side wall has an outwardly bent portion defining with the remainder of said last mentioned foremost part a slot which constitutes said socket.

* * * * *